United States Patent [19]

Hochman et al.

[11] Patent Number: 5,438,989

[45] Date of Patent: Aug. 8, 1995

[54] SOLID TUMOR, CORTICAL FUNCTION, AND NERVE TISSUE IMAGING METHODS AND DEVICE

[76] Inventors: Darryl Hochman, 22933 Edmonds Way, Edmonds, Wash. 98020; Michael M. Haglund, 1647 N. 197th Pl., Seattle, Wash. 98133

[21] Appl. No.: 894,270

[22] Filed: Jun. 8, 1992

Related U.S. Application Data

[63] Continuation-in-part of Ser. No. 565,454, Aug. 10, 1990, Pat. No. 5,215,095.

[51] Int. Cl.$^6$ .......................... A61B 5/00; G01N 21/00
[52] U.S. Cl. .................................. 128/653.1; 128/654; 128/664; 128/665; 348/68; 348/77; 348/164; 364/413.13
[58] Field of Search ...................... 128/633, 653.1, 664, 128/665, 654; 382/6; 358/98, 110, 111, 113; 364/413.13; 348/65, 162, 164, 68, 69, 77

[56] References Cited

U.S. PATENT DOCUMENTS

| | | |
|---|---|---|
| 4,515,165 | 5/1985 | Carroll ................. 128/664 |
| 4,556,057 | 12/1985 | Hiruma et al. ............. 128/634 |
| 4,767,717 | 8/1988 | Baisden ............... 128/653.1 |
| 4,768,513 | 9/1988 | Suzuki ................. 128/665 |
| 4,852,579 | 8/1989 | Gilstad ................ 128/665 |
| 4,930,516 | 6/1990 | Alfano et al. . |
| 4,999,614 | 3/1991 | Ueda et al. ............. 358/113 |
| 5,014,709 | 5/1991 | Bjelkhagen et al. ......... 128/665 |
| 5,027,817 | 7/1991 | John ................... 128/654 |
| 5,079,698 | 1/1992 | Grenier et al. .......... 364/413.13 |
| 5,119,815 | 6/1992 | Chance ................ 128/665 |
| 5,198,977 | 3/1993 | Salb . |
| 5,213,105 | 5/1993 | Gratton et al. ........... 128/665 |
| 5,215,095 | 6/1993 | Macvicar et al. .......... 128/665 |

FOREIGN PATENT DOCUMENTS 1026769  7/1983  U.S.S.R. ................. 128/653.1

OTHER PUBLICATIONS

"Microwave Absorption by Normal and Tumor Cells", *Science*, vol. 174, pp. 72–74.

Herbin et al.; "Automated Registration of Dissimilar Images: Application to Medical Imagery", pp. 77–88, 1989.

D'Orsi et al., in L. W. Bassett and R. H. Gold eds., *Breast Cancer Detection, Mammography and Other Methods in Breast Imaging*, 2nd ed., Grune & Stratton, Inc., 1987, pp. 169–177.

Grinvald et al., Proc. Natl. Acad. Sci. USA__:11559, 1991, "High resolution optical imaging of functional grain architecture in the awake monkey".

Ts'o et al., *Science* 249:417, 1990, "Functional Organization of Primate Visual Cortex Revealed by High Resolution Optical Imaging".

Frostig et al., *Proc. Natl. Acad. Sci. USA* 87:6082, 1990; "Cortical functional architecture and local coupling between neurol activity and the micro circulation revealed by in vivo high-resolution optical imaging of intrinsic signals".

*Primary Examiner*—Krista M. Pfaffle

[57] ABSTRACT

The present invention provides a method for imaging margins, grade and dimensions of solid tumor tissue located in an area of interest, comprising illuminating the area of interest with high intensity, emr (electromagnetic radiation) containing the wavelength of emr absorbed by a dye, obtaining a video signal of the area of interest as an averaged control image and processing the averaged control image into the averaged control frame, administering the dye by bolus injection into a vein circulating to the area of interest, obtaining a series of video images of the area of interest over time as subsequent images and processing each subsequent image as a subsequent frame, comparing each subsequent frame with the processed averaged control frame to obtain a series of difference images, and comparing each difference image for initial evidence of changed absorption within the area of interest which is the outline of solid tumor tissue, whereby tumor tissue is characterized by faster absorption of emr as a result of increased vascularity of solid tumor tissue and inability to clear the dye as fast as normal tissue.

9 Claims, 9 Drawing Sheets

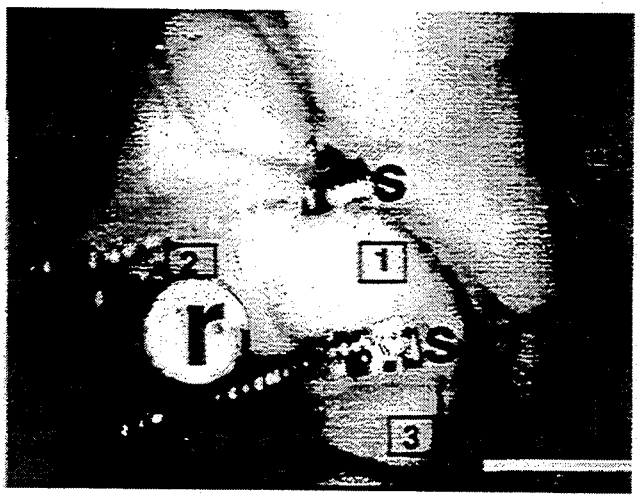
FIGURE 1A1
FIGURE 1A2
FIGURE 1A3
FIGURE 1A4

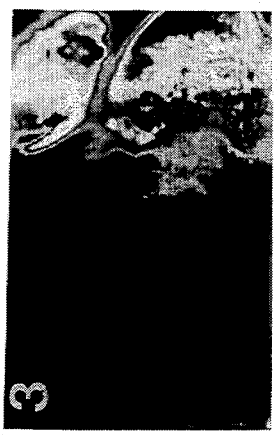
FIGURE 2A3
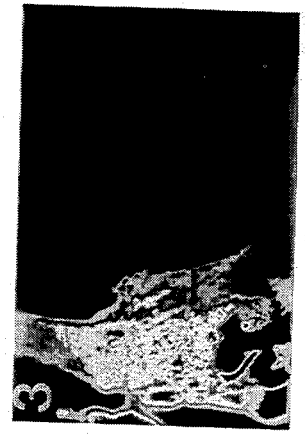
FIGURE 2B3
FIGURE 2A2
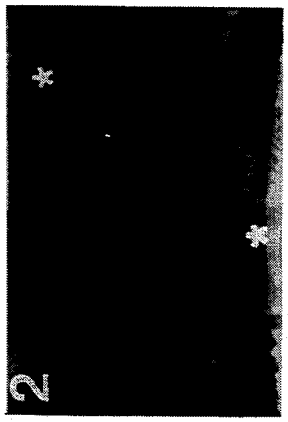
FIGURE 2B2
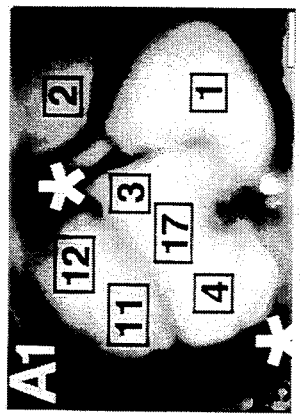
FIGURE 2A1
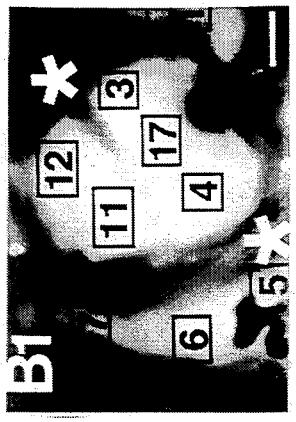
FIGURE 2B1

FIGURE 6A
FIGURE 6B
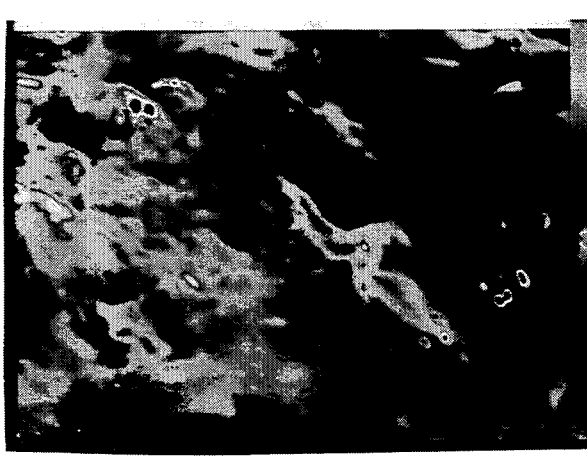
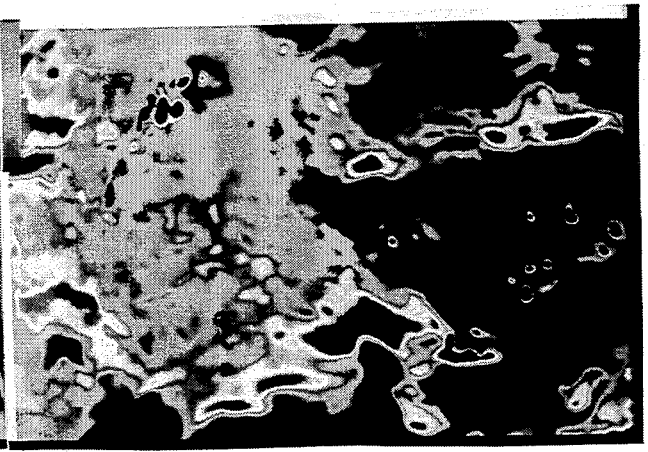
FIGURE 6C
FIGURE 6D

SOLID TUMOR, CORTICAL FUNCTION, AND NERVE TISSUE IMAGING METHODS AND DEVICE

CROSS-REFERENCE TO RELATED APPLICATION

This application is a continuation-in-part of U.S. patent application No. 07/565,454, filed Aug. 10, 1990, now U.S. Pat. No. 5,215,095.

TECHNICAL FIELD OF THE INVENTION

The present invention provides a method for real-time detection of solid tumor tissue, plus an ability to grade and characterize tumor tissue. The present invention further provides a method for real-time mapping of functional and dysfunctional cerebral cortex and nervous tissue. The present invention further provides a device for real-time detection and optical imaging for the inventive methods.

BACKGROUND OF THE INVENTION

A primary goal of neurological surgery is the complete removal of abnormal or pathological tissue while sparing normal areas. Hence, the neurosurgeon attempts to identify boundaries of pathological or dysfunctional tissue and to map adjacent areas of the cortex committed to important functions, such as language, motor and sensory areas so that pathological/dysfunctional tissue is removed without removing functional areas.

Incidence rates for primary intracranial brain tumors are in the range of 50-150 cases per million population or about 18,000 cases per year (Berens et al. 1990). Approximately one half of brain tumors are malignant. The incidence of malignant brain tumors in adults is predominantly in the age range of 40-55 years while the incidence of more benign tumors peaks near 35 years of age. A primary means for treatment of such tumors is surgical removal. Many studies have shown that when more of the total amount of tumor tissue is removed, the better the clinical outcome. For gross total resections of tumors, the 5-year survival rate is doubled when compared to subtotal resection. Both duration of survival and independent status of the patient are prolonged when the extent of resection is maximized in malignant gliomas.

Of the 500,000 patients projected to die of systemic cancer per year in the United States, approximately 25%, or over 125,000 can be expected to have intracranial metastasis. The primary focus for surgery in this group is in those patients with single lesions who do not have widespread or progressive cancer. This group represents about 20-25% of patients with metastases (30,000), however, the actual number of patients that are good candidates for surgery is slightly smaller. Of those patients undergoing surgery, one half will have local recurrence of their tumor at the site of operation, while the other half will develop a tumor elsewhere. The fact that about 50% of the surgeries fail at the site of operation means that an improved ability to remove as much tumor as possible by detecting and localizing tumor margins during tumor removal could potentially decrease the incidence of local recurrence.

Thus, for both primary and metasiatic tumors, the more tumor tissue removed, the better the outcome and the longer the survival. Further, by maximizing the extent of resection, the length of functional, good quality survival is also increased.

Most current tumor imaging techniques are performed before surgery to provide information about tumor location. Presurgery imaging methods include magnetic resonance imaging (MRI) and computerized tomography (CT). In the operating room, only intraoperative ultrasound and stereotaxic systems can provide information about the location of tumors. Ultrasound shows location of the tumor from the surface but does not provide information to the surgeon once surgery begins to prevent distruction of important functional tissue while permitting maximal removal of tumor tissue. Stereotaxic systems coupled with advanced imaging techniques have (at select few hospitals) been able to localize tumor margins based upon the preoperative CT or MRI scans. However studies (Kelly, 1990) have shown that the actual tumor extends 2-3 cm beyond where the image enhanced putative tumor is located on preoperative images. Therefore, the only current reliable method to determine the location of tumors is by sending biopsies during surgery (i.e., multiple histological margin sampling) and waiting for results of microscopic examination of frozen sections. Not only is it not advisable to continually take breaks during surgery, but such biopsies are, at best, an estimation technique and are subject to sampling errors and incorrect readings as compared to permanent tissue sections that are available about one week later. Thus, a surgeon often relies upon an estimation technique as a guide when patient outcome is dependent upon aggressive removal of tumor tissue. Surgeons have difficult decisions between aggressively removing tissue and destroying surrounding functional tissue and may not know the real outcome of their procedure until one week later and this may require an additional surgical procedure.

Multiple histological margin sampling suffers several drawbacks. First this is a time-consuming procedure as it can add about 30 to 90 minutes (depending upon the number of samples taken) to a surgical procedure when the patient is under anesthesia. Second, this procedure is prone to errors as a pathologist must prepare and evaluate samples in short order. Third, it is certainly the case that margin sampling does not truly evaluate all regions surrounding a primary tumor as some areas of residual tumor can be missed due to sampling error. Fourth, increased time for margin sampling is expensive as operating room time costs are high and this leads to increased overall medical costs. Moreover, increased operating room time for the patient increases the probability of infection.

Other techniques developed to improve visual imaging of solid tumor masses during surgery include determining the shape of visible luminescence spectra from normal and cancerpus tissue. According to U.S. Pat. No. 4,930,516, in cancerpus tissue there is a shift to blue with different luminescent intensity peaks as compared to normal tissue. This method involves exciting tissue with a beam of ultraviolet (UV) light and comparing visible native luminescence emitted from the tissue with a historical control from the same tissue type. Such a procedure is fraught with difficulties because a real time, spatial map of the tumor location is not provided for the use of a surgeon. Moreover, the use of UV light for an excitation wavelength can cause photodynamic changes to normal cells, is dangerous for use in an operating room, and penetrates only superficially into tissue and requires quartz optical components instead of glass.

Therefore, there is a need in the art for a more comprehensive and faster technique and a device for assisting such a technique to localize for solid tumor locations and map precise tumor margins in a real-time mode during surgery. Such a device and method should be further useful for inexpensive evaluation of any solid tumor (e.g., breast mammography) by a noninvasive procedure and capable of grading and characterizing the tumors.

A type of neurosurgical procedure which also exemplifies these principles is the surgical treatment of intractable epilepsy (that is, epilepsy which cannot be controlled with medications). Presently, electroencephalography (EEG) and electrocorticography (ECoG) techniques are used prior to and during surgery for the purposes of identifying areas of abnormal brain activity, such as epileptic foci. These measurements provide a direct measurement of the brain's electrical activity.

Intraoperative EEG techniques involve placing an array of electrodes upon the surface of the cortex. This is done in an attempt to localize abnormal cortical activity of epileptic seizure discharge. Although EEG techniques are of widespread use, hazards and limitations are associated with these techniques. The size of the electrode surface and the distance between electrodes in an EEG array are large with respect to the size of brain cells (e.g., neurons) with epileptic foci. Thus, current techniques provide poor spatial resolution (approximately 1.0 cm) of the areas of abnormal cortical activity. Further, EEG techniques do not provide a map of normal cortical function in response to external stimuli (such as being able to identify a cortical area dedicated to speech, motor or sensory functions by recording electrical activity while the patient speaks). A modification of this technique, called cortical evoked potentials, can provide some functional cortical mapping. However, the cortical evoked potential technique suffers from the same spatial resolution problems as the EEG technique.

The most common method of intraoperative localization of cortical function in epilepsy and tumor surgery is direct electrical stimulation of the cortical surface with a stimulating electrode. Using this technique, the surgeon attempts to evoke either an observed motor response from specific parts of the body, or in the case of an awake patient, to generate specific sensations or cause an interruption in the patient's speech output. Again, this technique suffers from the same problems as the EEG technique because it offers only crude spatial localization of function.

Possible consequences of the inaccuracies of all these techniques, when employed for identifying the portion of the cortex responsible for epileptic seizures in a patient, are either a greater than necessary amount of cortical tissue is removed possibly leaving the patient with a deficit in function, or that not enough tissue is removed leaving the patient uncured by the surgery. Despite these inadequacies, such techniques have been deemed acceptable treatment for intractable epilepsy. The same principles apply to tumor surgeries, however, intraoperative functional mapping is not performed routinely.

In the past few years, researchers have been using imaging techniques in animal models to identify functional areas of cortex with high spatial resolution. One type of such technique uses a voltage-sensitive dye. A voltage-sensitive dye is one whose optical properties change during changes in electrical activity of neuronal cells. The spatial resolution achieved by these techniques is near the single cell level. Blasdel and Salama (*Nature* 321:579, 1986) used a voltage-sensitive dye (merocyanine oxazolone) to map cortical function in a monkey model. The use of these kinds of dyes would pose too great a risk for use in humans in view of their toxicity. Further, such dyes are bleached by light and must be infused frequently.

Recently, measurement of intrinsic signals have been shown to provide similar spatial resolution as voltage-sensitive dye imaging. Intrinsic signals are light reflecting changes in cortical tissue partially caused by changes in neuronal activity. Unlike other techniques used for imaging neuronal activity, imaging intrinsic signals does not require using dyes (which are often too toxic for clinical use) or radioactive labels. For example, Grinvald et al. (*Nature* 324:361, 1986) measured intrinsic changes in optical properties of cortical tissue by reflection measurements of tissue in response to electrical or metabolic activity. Light of wavelength 500 to 700 nm may also be reflected differently between active and quiescent tissue due, to increased blood flow into regions of higher neuronal activity. Another aspect which may contribute to intrinsic signals is a change in the ratio of oxyhemoglobin to deoxyhemoglobin.

Ts'o et al. (*Science* 249:417, 1990) used a charge-coupled device (CCD) camera to detect intrinsic signals in a monkey model. However, this technique would not be practical in a clinical environment because imaging was achieved by implanting a stainless steel optical chamber in the skull and in order to achieve sufficient signal to noise ratios, Ts'o et al. had to average images over periods of time greater than 30 minutes per image. By comparison to all other known techniques for localizing cortical function, imaging intrinsic signals is a relatively non-invasive technique.

Mechanisms responsible for intrinsic signals are not well understood, possible sources of intrinsic signals include dilatation of small blood vessels, increased scattering of light from neuronal activity-dependent release of potassium, or from swelling of neurons and/or glial cells.

None of the experimental procedures provide a feasible and safe technique for real-time optical functional imaging of cortical activity in a surgical setting to accurately and precisely identify pathological/dysfunctional cortical areas during surgical procedures. Therefore, there is a need in the art for a procedure and apparatus for real-time optical imaging of cortical tissue which can precisely and quickly distinguish normal and abnormal cortical tissue. There is also a need in the art for developing a method that can image intrinsic signals with high spatial resolution, provide immediate images and be compatible with normal procedures in the operating room. This invention was made, in part, in an effort to satisfy this need.

SUMMARY OF THE INVENTION

The inventive method and device can be used to identify, grade and characterize solid tumors by imaging changes in electromagnetic absorption which reflects dynamics of dye perfusion through tissue. Further, the inventive method and device can be used to identify areas of neuronal activity during neurosurgical procedures. In particular, this invention can be used by a neurosurgeon intraoperatively to identify areas in the brain dedicated to important functions such as vision, movement, sensation, memory and language. Further the present inventive method and device can be used to detect areas of abnormal cortical activity, such as epileptic foci. Lastly, the present invention can be used to identify individual nerves during neurosurgical procedures for tumor removal or anastamoses of severed nerves.

The present invention provides an apparatus for imaging tumor tissue or for real-time surgical imaging of cortical intrinsic signals or visualizing margins of solid tumor tissue, comprising, a means for obtaining a series of analog video signals, and a means for processing the analog video signals into either an averaged control image or a subsequent averaged image, a means for acquiring and analyzing a plurality of subsequent images and averaged control images to provide a difference image, wherein the difference image is processed to account for movement and noise and to amplify the changes across a dynamic range of the apparatus, and a means for displaying the difference image alone or superimposed over an analog video image.

The present invention further provides a method for imaging tumor margins and dimensions of solid tumor tissue located in an area of interest, comprising illuminating the area of interest with spatially even, intensive and non fluctuating light containing a wavelength of electromagnetic radiation (emr) (e.g., light) absorbed by a dye, obtaining a video signal of the area of interest as a series of frames and processing the the series of frames into an averaged control image, administering the dye by bolus injection into vasculature circulating to the area of interest, obtaining a subsequent series of frames of the area of interest over time and processing the subsequent series of frames into a subsequent averaged image, comparing each subsequent averaged image with the averaged control image to obtain a series of difference images, and comparing each difference image for initial evidence of changed absorption within the area of interest which is the outline of solid tumor tissue, whereby tumor tissue is characterized by different kinetics of dye uptake compared to normal tissue and a temporally changed pattern of altered absorption of light as a result of increased vascularity of solid tumor tissue. A preferred dye is indocyanine green which has a broad absorption wavelength range and a peak absorption in the range of 730 nm to 840 nm.

The present invention further comprises a method in real-time for optically imaging functional areas of interest of the cortex in a patient comprising illuminating the area of interest with high intensity emr containing near-infrared wavelengths of emr, obtaining a series of frames of the area of interest and processing the series of frames into an averaged control image, administering a stimulus paradigm to the patient to stimulate an intrinsic signal, obtaining a series of subsequent frames of the area of interest over time and processing the subsequent series of frames into a subsequent averaged image, comparing each subsequent averaged image with the averaged control image to obtain a series of difference images, and comparing each difference image for initial evidence of an intrinsic signal within the area of interest, whereby an intrinsic signal is characterized by a change in emr reflectance properties manifest as a signal in the difference image.

The present invention further includes a method for imaging damage to a peripheral or cranial nerves comprising: (a) illuminating an area of interest with high intensity emr, wherein the area of interest comprises the peripheral nerve of interest including the suspected site of damage and a region adjacent of the suspected site of damage; (b) obtaining a series of frames of the area of interest and processing the series of frames into an averaged control image; (c) Stimulating the peripheral or cranial nerve at a site adjacent of the suspected damaged site; (d) obtaining a series of subsequent frames at the time of stimulation and processing the series of subsequent frames into a subsequent averaged image; and (e) obtaining a difference image by subtracting the averaged control image from the subsequent averaged image to visualize the active region of the peripheral or cranial nerve, whereby nerve blockage is visualized as the point along the nerve where the intrinsic signal from the stimulated nerve abruptly ends, or is altered, attenuated or diminished in the difference image.

The present invention further includes a method for imaging tumor tissue surrounding or adjacent to nerve tissue to aid in selective resection of tumor tissue without destroying nerve tissue, comprising: (a) illuminating an area of interest with high intensity emr containing wavelength of emr absorbed by a dye; (b) obtaining a series of frames of the area of interest and processing the series of frames into an averaged control image; (c) stimulating the nerve; (d) obtaining a series of subsequent nerve frames and processing the subsequent series of nerve frames into a subsequent nerve averaged image; (e) obtaining a nerve difference image by subtracting the nerve averaged control image from the nerve subsequent averaged image to visualize the active nerve; (f) administering a dye into an artery feeding the area of interest; (g) obtaining a series of tumor subsequent frames and processing the tumor subsequent series of frames into a tumor subsequent averaged image; and (h) obtaining a tumor difference image by subtracting the; tumor averaged control image from the tumor subsequent averaged image to create a tumor difference image that is capable of visualizing the tumor. Further, the tumor difference image and the nerve difference image can be superimposed upon each other to simultaneously visualize the relative locations of tumor tissue and nervous tissue.

The present invention further comprises a method for enhancing sensitivity and contrast of the images obtained from tumor tissue or intrinsic signal difference images, comprising: (a) illuminating an area of interest with a plurality of wavelengths of emr, wherein there is at least a first wavelength of emr and a second wavelength of emr; (b) obtaining a sequence of frames corresponding to each wavelength of emr, wherein a first sequence of frames is from the first wavelength of emr, the second sequence of frames is from the second wavelength of emr and so on; (c) processing the first sequence of frames into a first averaged control image, the second sequence of frames into a second averaged control image and so on; (d) stimulating for intrinsic signals or administering a dye for tumor tissue imaging; (e) obtaining a first series of subsequent frames using the first wavelength of emr, a second series of subsequent frames using the second wavelength of emr, and so on, and processing the first, second and so on subsequent series of frames into the first, second and so on subsequent averaged images, respectively; (f) obtaining a first difference image by subtracting the first averaged control image from the first subsequent averaged image and a second difference image by subtracting the second averaged control image from the second subsequent averaged image, and so on; and (g) obtaining an enhanced difference image by ratioing the first difference image to the second difference image. Preferably, the monochromatic emr sources to illuminate the area of interest are from laser sources. This technique is useful for obtaining three dimensional information of the area of interest.

BRIEF DESCRIPTION OF THE DRAWINGS

The file of this patent application contains at least one drawing executed in color. Copies of the is patent with color drawings will be provided by the Patent and Trademark Office upon request and payment of the accessary fee.

FIG. 1, A2 shows the percentage difference image representing baseline activity between two controls before stimulation.

FIG. 1, A3 represents an image (4 sec average, 128 frames) obtained immediately after stimulation (4 sec, 6 mA). This stimulation was followed by the shortest of the four afterdischarge episodes (bottom left trace of FIG. 1B). The black cortical areas surrounding the cator areas represent regions where the optical changes are below baseline.

FIG. 1, A4 represents an image (4 sec average, 128 frames) obtained immediately after stimulation #4 (4 sec, 8 mA). This stimulation elicited the longest of the four afterdischarge episodes (bottom right trace of FIG. 1B).

FIG. 2 shows anterior-left, posterior-right, superior-top, and Sylvan fissure-bottom images of a human brain. Asterisks on the cortical surface serve as reference points between 2A1 and 2B1. The scale bar is again equal to 1 cm. In A 1, the numbered boxes represent sites where cortical stimulation evoked palate tingling (1), tongue tingling (2), speech arrest-Broca's areas (3,4) and no response (11, 12, 17). During three trials, an image was averaged (1 sec, 32 frames) and stored (1 sec) every 2 sec at rest, during 40 sec of tongue movement, and during recovery. The closed arrowhead shows when tongue movement began and open arrowheads when the movement stopped.

In FIG. 2, A2 a percentage difference image was taken from two cortical images before tongue movement. Open circle on the time line in FIG. 2C shows the times at which the averaged control images were taken. The image shows some noise about the baseline at rest. The magnitude of optical change for all images of FIG. 2 is represented by the pseudocolor scale.

FIG. 2, A3 shows the percentage difference image during tongue movement. The filled circle on time line

FIG. 2, B1 shows the cortical surface from the same patient as is shown in all images of FIG. 2 with the image moved anteriorly to incorporate more of the premotor cortex (asterisks at the same sites in A1-2 and B1-2). In other premotor sites (#5, #6, #7), no change in language was found during cortical stimulation. The patient viewed blank slides (control) and then named slides of objects which were presented every 2 seconds (2B2, 2B3). The percentage difference images during naming comparing control image (2B2) to the optical changes during naming (2B3) are shown. Circles on the time line (2D) represent when the control image (B2, open circle) and naming image (B3, closed circle) were obtained. The maximum optical changes during naming are in the premotor region and not in the area activated by tongue movement without speech.

FIG. 2C shows the average percentage difference change from each of four areas with positive responses to cortical stimulation mapping. The changes in the four areas were repeatable and the largest change in the positive direction was from the palate sensory cortex (site #1).

The average percentage changes from two sites considered essential for language (sites #1 and #2) and secondary sites (#3, #4, and #5) are shown in FIG. 3C. All five sites show optical changes compared to six more anterior sites that were not critical for language function.

FIG. 6 is a series of images and difference images of an area of interest where a tumor was resected and biopsies were taken for multiple histological margin sampling. The area of interest was thought to be free of tumor during the procedure. Normally, in this size of a resection margin, only a single frozen sample would be taken for pathology analysis. In this case, while the surgeon was waiting for a pathology report based upon frozen sections (standard procedure), the images shown in FIG. 6 were obtained. FIG. 6A (upper left) is an analog image of the area of interest and FIG. 6B (upper right) shows the area of interest with histological markers. FIG. 6C (lower left) shows the post dye difference image taken at one minute and at 10 minutes (FIG. 6D, lower right). Both post dye difference images show a number of positive sites. This procedure is described in Example 4.

DETAILED DESCRIPTION OF THE INVENTION

Figure 1B:
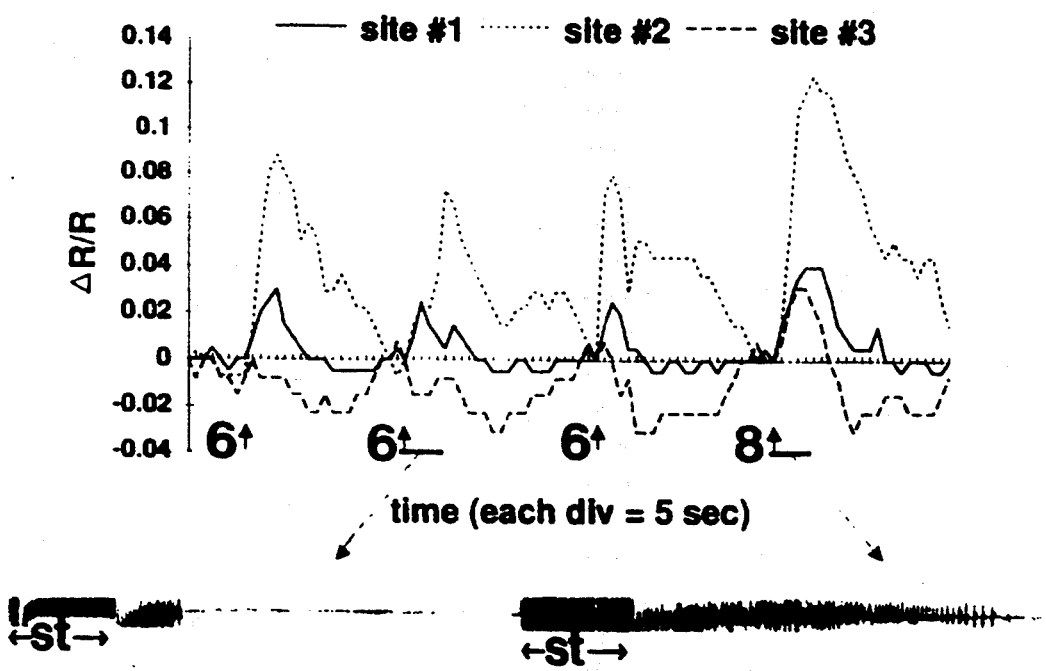
FIG. 1, A2 illustrates a view of a human cortex just anterior to face-motor cortex with one recording (R) and two stimulating electrodes (s), and three sites (#1, #2, #3) where average percent changes were determined. The scale bar equals 1 cm. Averages of 128 images (4/sec) were acquired at 30 Hz and stored (1/sec). After acquiring 3-6 averaged control images (5 sec/image), a bipolar cortical stimulation evoked epileptiform afterdischarge activity.
FIG. 1E (middle right) is one minute after dye administration and FIG. 4F (lower right) is five minutes after dye administration showing complete dye clearance in this low grade tumor. These data show that tumor tissue takes up dye faster. Therefore, it is possible to image even low grade tumors by the inventive apparatus.

The present invention provides an apparatus for imaging neuronal intrinsic signals in real time and for determining the presence, size, margins, dimensions, and grade of a solid tumor mass using a dye. The present invention further provides a method for functional mapping of the cortex in a patient by mapping intrinsic signals in real time, a method for determining the presence, size, location, and grade of solid tumor tissue in real time without the sampling errors of biopsies or the delay of and possible misdiagnosis of the pathologist's frozen section analysis, and a method for imaging nerve tissue that may be physically damaged or surrounded by and adjacent to tumor cells. The inventive methods employ a similar apparatus, comprising a series of components, including video input hardware and dedicated image processing hardware. The video input hardware is, for example, a photo-detector, such as a CCD (charge coupled device) camera (preferably a COHU 6510 CCD Monochrome Camera with a COHU 6500 electronic control box made by COHU Electronics San Diego, Calif.). In some cameras the analog signal is digitized 8-bits deep on an ADI board (analog-to-digital board). The dedicated image processing hardware is generally a "host computer". The host computer is any common general computer (such as an IBM PC type or Sun SPARC) that is interfaced with imaging hardware and sends commands to the imaging hardware that direct data flow, computations, image acquisition and the like. Thus, the host computer directs the actions of the imaging hardware and provides the user interface.

Definitions

The following are definitions of commonly used terms and that are applied in this application according to their art-accepted usage, such as described in Inoue, *Video Microscopy* Plenum Press, New York, 1989.

Area of Interest is that area of tissue that comprises the subject of the image.

Arithmetic Logic Unit (ALU) is the hardware component that performs a variety of mathematical and logic operations (e.g., sum, difference, exclusive or, multiply by a constant, etc.) on the image signal at extremely high speeds.

Averaged Control Image is that updateable image that is the average of a series of real time images over a period of time.

Charge Coupled Device (CCD) is a photo-sensitive silicon chip used in place of a pickup tube in miniature video cameras.

Difference Image is the manipulated image created by adding or subtracting a subsequent image or a particular image in time from an averaged control image.

Frame is a single digitized array of single video pictures.

Frame Buffer is a piece of hardware that serves as a temporary storage of a frame, such as an averaged control image, a subsequent image or a difference image.

Geometric Transformation (Gonzalez and Wintz, *Digital Image Processing*, Addison-Wesley Publishing Co., Reading, 1987) generally modify spatial relationships between pixels in an image. For this reason, geometric transformations are often called "rubber sheet transformations" because they can be viewed as the process of "printing" an image on a sheet of rubber and stretching this sheet according to a predefined set of rules. As applied to video imaging, subsequent images can be viewed as having been distorted due to movement and it is desirable to "warp" these images so that they are similar to the control images. Geometric transformations are distinguished from "point transformations" in that point transformations modify a pixel's value in an image based solely upon that pixel's value and/or location and no other pixel values are involved in the transformation.

Image is a frame or composition of frames that have been altered after digitization, such as processing a sequence of frames into an averaged control image or a subsequent averaged image.

Intrinsic Signal means a detectable change in reflectance properties of neuronal tissue due to endogenous physiologic activity. Possible causes of intrinsic signals include, for example, membrane depolarization; glial cell swelling, ion flux across neuronal membranes, blood volume changes, blood oxygenation (hemoglobin to oxyhemoglobin), tissue oxygenation and combinations thereof.

Linear Histogram Stretch is a transformation in which the values between two points (high, low) are reinappeal to cover a full range of values (i.e., dynamic range). For example, the low value is mapped to zero, the high to 255, and the intermediate values are mapped to linearly increasing brightness values. All brightness values below the low value are set to zero and all brightness values above the high value are set to the high value.

Look Up Table (LUT) is a piece of hardware that functions to store memory that directs conversion of the gray value of each pixel into another gray value or color that is specified by the LUT. The LUT can be programmed to manipulate image contrast, threshold an image, apply pseudocolor and the like (such as a convenient implementation method for point processing algorithms). In the case of the present invention, the LUTs are, preferably, implemented for speed on an ADI and/or ALU boards.

Paradigms cause a change in electrical activity of an area of cortical tissue dedicated to a specific function (e.g., speech, language, vision, etc.) thus causing an increase or decrease in what is called an intrinsic signal.

Pixel is the individual units of image in each frame of the digitized signal. The intensity of each pixel is linearly proportional to the intensity of illumination before signal manipulation and corresponds to the amount of emr (photons) being reflected from a particular area of tissue corresponding to a particular pixel. It should be noted that an image pixel is the smallest unit of a digital image and its output intensity can be any value. A CCD pixel is the smallest detecting element on a CCD chip and its analog output is linearly proportional to the number of photons it has detected.

Processed Difference Image is the raw difference image that has been processed or manipulated to filter out noise or movement and increase the dynamics of effect of different pixel values to illustrate events in the area of interest.

Tumor Margin is the area where the surgeon has resected the tumor.

Apparatus

The inventive apparatus is made as one unit or a group of components. The first component is a high intensity emr source. The emr source is for illuminating the cortical surface or area of interest, such as an area suspected of having solid tumor tissue. Different intrinsic signals can be illuminated by different wavelengths of emr. Moreover, the emr source must include the wavelengths of emr absorbed by the dye for the tumor imaging method. For example, when the dye is indocyanine green, preferred wavelengths are from about 730 nm to about 840 nm. For other dyes, the preferred wavelengths of illuminating emr should include wavelengths at which the dye absorbs. The term emr instead of light is used because it is also possible to image in the infrared region of the spectrum outside of the visible light range.

When determining intrinsic signals from the cortex, reflected emr can be filtered to allow for video imaging of only selected wavelengths of emr. Preferred selected wavelengths of emr include, for example, from about 500 nm to about 900 nm, or most preferably, the near infrared spectrum. Generally, longer wavelengths (e.g., approximately 800 nm) measure deeper cortical activity.

Moreover, that part of the infrared spectrum in an invisible range of between 0.75 to about 1000 micrometers allows for a determination of intrinsic signals through dura and skull, thereby allowing for a determination of intrinsic signals through intact skull and dura and without the risks associated with neurosurgery. When using this range of far infrared wavelengths, an IR detector is a different device than a CCD chip for a visible analog camera. IR detectors are made from materials such as indium arsenide, germanlure and mercury cadmium telluride rather than silicon. IR detectors must be cryogenically cooled in order that they be sensitive to small changes in temperature. For example, one IR imaging system is an IRC-64 infrared camera (Cincinnati Electronics, Mason Ohio).

As heat reaches the surface of the cortex, it emits electromagnetic radiation in the range of about 3–5 or 8–14 microns. Others have attempted to image this emitted radiation (see, for example, Gorbach et al., "Infrared Mapping of the Cerebral Cortex" *Thermography* 3:108, 1989). However, according to the present invention these emitted wavelengths are filtered out and an IR detector instead of a CCD detector is used. An IR emr source is, for example, a Tunable IR Diode Laser from Laser Photonics, Orlando, Fla. The imaged wavelengths are different from body heat and images of changes in absorption and emr scattering can be obtained according to the inventive method. In the case of tumor images through intact skin and possibly bone, a dye that absorbs in the IR can be used (e.g., indocyanine green). Other useful dyes include, for example, Photofrin ® derived from a hematoporphyrin derivative (HPD) and absorbs light at 630 nm, mono espatyl chlorin-36 (NPe$_6$, Nippon Petrochemical, Japan), benzoporphyrin derivative (BPD, Quadra Logic Vancouver BC), and combinations thereof.

Preferably, the emr source, is a high intensity, broad spectrum emr source, such as a tungsten-halogen lamp and a cutoff filter for all wavelengths below 695 nm. Most preferably, the emr source is directed to the area of interest by a fiber optic means. An example of such a emr source is a fiber optic emr passing through a beam splitter, controlled by a D.C. regulated power supply (Lambda, Inc.) and passed through a 695 nm longpass filter.

The inventive apparatus includes a means for obtaining an analog video signal of the cortex or area of interest. A preferred device for obtaining an analog video signal is a charge coupled device (CCD) video camera which creates an output video signal at 30 Hz having, for example, 512 horizontal lines per frame using standard RS 170 convention. One such device is a CCD-72 Solid State Camera (Dage-MTI Inc., Michigan City Ind.) and another such device is a COHU 6500 (COHU, San Diego Calif.).

The area of interest must be evenly illuminated to better adjust the signal over a full dynamic range. If there is uneven illumination in the area of interest, it will limit the dynamic range. Preferably a high intensity and diffuse or even lighting system is used. Techniques to obtain even illumination over the area of interest include, for example, diffuse lighting, image processing algorithms to compensate for uneven illumination on a digitized image, a constant shade gray image marker point in the area of interest as a control point, a wavelength cutoff filter in front of the camera and/or emr source, or combinations thereof. Preferably, a regulated power supply will prevent fluctuations in emr sources. A footplate system is an optical glass (sterile) contacting and covering the area of interest to provide a flatter contour. The footplate also retards tissue movement.

The analog signal must first be adjusted to maximize sensitivity of detection (at the level of the analog signal and before digitizing) to amplify the signal and spread the signal across the full possible dynamic range, thereby increasing sensitivity of the apparatus. 60 Hz noise (such as from A.C. power lines) is filtered out in the camera control box by an analog filter. Such adjustments further serve to enhance, amplify and condition the analog signal from the CCD. One means for properly adjusting the input analog signal is to digitize this signal at video speed (30 Hz), and view the area of interest as a digitized image that is converted back to analog.

It is important to compensate for small movements of tissue or the patient during the imaging process. Larger patient-movements require a new orientation of the camera and obtaining a new averaged control image. Compensating for movement can be done by mechanical or computational means or both. Mechanical means include, for example, placing a footplate over the area of interest wherein the footplate comprises sterilized optical quality glass in a framing device, and/or securing the camera and possibly the emr source to the skeletal frame of the patient, and combinations of both. When the camera and/or emr source are attached to the skeletal structure of the patient, any patient movements will not effect the image because the camera and illumination source will remain in a constant orientation to the area of interest. The advantage of the footplate is that it retards tissue movement caused by arterial pressure and/or respiration and prevents changes due to evaporation of cerebrospinal fluid. Computational means include, for example, using functional control points in the area of interest and triangulation-type algorithms to compensate for movements of these control or tie points, and "image warping" techniques whereby each subsequent image is registered geometrically to the averaged control image to compensate for movement, and combinations of both techniques. The image warping technique is described in, for example, Wolberg, "Digital Image Warping" IEEE Computer Society Press, Los Alimitos, Calif. 1990. The image warping technique can further indicate when movement has become too great for the averaged control image and that a new averaged control image must be taken. Control points can be placed directly in the area of interest, such as directly on the cortical surface for intrinsic signal analysis. For example, Goshtasby ("Piecewise Linear Mapping Functions for Image Registration" in *Pattern Recognition* vol. 19 pp 459–66, 1986) describes a method whereby an image is divided into triangular regions using control points. A separate geometrical transformation is applied to each triangular region to spatially register each control point to a corresponding triangular region in a control image.

The analog video signal is continuously fed into a means for processing the signal. One such means for acquiring and analyzing data is an image analyzer (e.g., Series 151 Image Processor, Imaging Technologies, Inc. Woburn Mass.). An image analyzer can receive and digitize an analog video signal with an analog to digital interface and perform such a function at a frame speed of about 1/30th of a second (e.g., 30 Hz or "video speed"). Processing the signal involves first digitizing the signal into a series of pixels or small squares assigned a value (in a binary system) dependent upon the number of photons (i.e., quantity of emr) being reflected off tissue from the part of the area of interest assigned to that pixel. For example, in a standard 512×512 image from a current technology CCD, there would be 262,144 pixels per image. In an 8 bit system, each pixel is represented by 8 bits. One can cool the CCD to reduce thermal noise.

Preferably, the signal processing means includes a programmable look-up table (e.g., CMI50-LUTI6, Imaging Technology, Woburn Mass.) initialized with values for converting gray coded pixel values, representative of a black and white image, to color coded values based upon the intensity of each gray coded value. This provides image enhancement via an image stretch. An image stretch is a technique whereby the highest and lowest pixel intensity values used to represent each of the pixels in a digital image frame are determined over a region of the image frame which is to be stretched. Stretching a selected region over a larger range of values permits, for example, easier identification and removal of relatively high, spurious values due to noise (e.g., glare).

Each image received is stored in the frame buffer, preferably within the context of a CPU as a frame of data elements represented, for example, as a 512 by 512 array of pixels. Each pixel has a 8 bit value corresponding to one of 256 levels of gray.

The processing means further includes a plurality of frame buffers having frame storage areas for storing frames of digitized image data received from the A/D interface. The frame storage area comprises at least one megabyte of memory space, and preferably at least 8 megabytes of storage space. An additional 16-bit frame storage area is preferred as an accumulator for storing processed image frames having pixel intensities represented by more than 8-bits. The frame buffers are temporary fast memory. The processing means should include at least three frame buffers. One is for storing the averaged control image, another is for storing the subsequent image and a third is for storing a difference image between the averaged control image and the subsequent image.

The processing means further includes an arithmetic logic unit (ALU) (e.g., ALU-150 Pipeline Processor) for performing arithmetical (add, subtract, etc.) and logical (and, or, etc.) functions from data located in one or more frame buffers. An ALU is a fast processor. The ALLY allows for image averaging in real time. For example, a newly incoming digitized image can be sent directly to the ALU and is added or subtracted to an averaged control image sitting in a frame buffer by passing both images through an ALU and adding them. After a last image is added, this 16 bit result can be sent again through an ALU which will divide this result by a constant (i.e., the total number of images). The output from the ALU is either stored in a frame buffer, sent for more processing, or used as its own input and again combined with another image.

It is important to compensate for patient movement in the digitized images before subtracting such images. Thus, geometric transformations are applied to the images so that they are geometrically registered prior to subtraction.

The inventive apparatus can enhance processing speed to create a difference frame by adding a real time modular processor or faster CPU chip to the image processor. For example, one real time modular processor is a 150 RTMP-150 Real Time Modular Processor (Imaging Technology, Woburn Mass.).

The processing means further may include a means for performing a histogram stretch of the difference frames (e.g., Histogram/Feature Extractor HF 151-I-V module, Imaging Technology, Woburn Mass.) to enhance each difference image across its dynamic range. A linear histogram stretch is described in, for example, Green, *Digital Image Processing: A Systems Approach,* Van Nostrand Reinhold, New York, 1983. A histogram stretch assigns the brightest pixel, or one with the highest value in the difference image and assigns this the maximum value. The smallest pixel value is assigned the minimum value and every other value in between is assigned a linear value (for a linear histogram stretch or a logarithmic value for a log histogram stretch, etc) in between the maximum and minimum values. This allows the difference image to fully utilize the full dynamic range which provide for absolute changes.

The difference image signal is, preferably, further processed to smooth out the image and remove high frequency noise. For example, a lowpass spatial filter can block high spatial frequencies and/or low spatial frequencies to remove high frequency noises at either end of the dynamic range. This provides a smoothed-out processed difference image (in digital format). The digitally processed difference image can be color-coded by assigning a spectrum of colors to differing shades of gray. This image is then converted back to an analog image (by an ADI board) and displayed for a real time visualization of differences between an averaged control image and subsequent images. Moreover, the processed difference image can be superimposed over the analog image to display regions upon a video display of the area of interest, those specific tissue sites where the dye may have a faster uptake or where an intrinsic signal may be occurring.

The present invention further includes a means for subtractive processing of difference images to identify cortical areas of neuronal inhibition. Normally areas of increased neuronal activity result in an increase of the emr absorption capacity of neuronal tissue (i.e., the tissue gets darker is visible light is used for emr illumination, or an intrinsic signal increases in a positive direction). Similarly, a decrease in neuronal activity results in a decrease of emr absorption capacity of the tissue (i.e., the tissue appears brighter, or intrinsic signals become negative). For example, image A is a subsequent averaged image and image B is an averaged control image. Normally, when a pixel in image A is subtracted from a pixel in image B and a negative value results, this value is treated as zero. Hence, difference images cannot account for areas of inhibition. However, the present invention provides a method for identifying both negative and positive intrinsic signals, by the method comprising: (a) subtracting image A (a subsequent averaged image) from image B (an averaged control image) to create a first difference image, whereby all negative pixel values are zero; and (b) subtracting image B from image A to create a second difference image whereby all negative pixel values are zero; and adding the first and second difference images to create a "sum difference image". The sum difference image shows areas of increased activity (i.e., color coded with warmer colors such as yellow, orange, red) and show areas of less activity or inhibition (i.e., color coded with colder colors such as green, blue, purple). Alternatively, one can overlay the first difference image on the second difference image. Either method provides an image of increased neuronal activity and decreased neuronal activity.

Preferably, the processing means further includes an optical disk for storing digital image data, a printer for providing hard copy of the digital and/or analog video image and a monitor to provide for the physician to continuously monitor the difference frame output (converted back to an analog signal) of the apparatus. The difference frame output may be superimposed upon the real time analog video image to provide a video image of the area of interest (e.g., cortical surface or suspected tumor site) superimposed with a color-coded difference frame, in frozen time, to indicate where regions of faster dye uptake have occurred and where there are intrinsic signals in response to some stimulus or paradigm.

During a surgical procedure, there is often patient movement. In the case of an anesthetized patient, motion is often due to respiration and blood flow. In an awake patient, there will be additional movement. Movement must be compensated for in the digitized images so that the images are geometrically registered prior to subtraction. Geometric compensation is achieved by applying geometric transformations to the digitized images. One piece of image-processing hardware which can accomplish geometric transformations in real-time is a GP-150 Geometrical Processor board (Informatique et Techniques Avancees, Issy-les-Moulineaux, France. The GP-150 Processor board is compatible with Itex hardware and performs real time rotations, translations, zooms, and second degree distortion corrections at video rates with bilinear interpolation on $512 \times 512 \times 8$-bit images.

Imaging Methods

The method for imaging a solid tumor involves periodically administering a dye by bolus injection into vasculature (e.g., artery or vein) perfusing the suspected tumor site in the area of interest. The video CCD of the inventive apparatus is focused upon the suspected solid tumor site (area of interest) and high intensity emr containing the wavelength absorbed by the dye illuminates the site. Just prior to administration of the dye, the first averaged image is taken, digitized and stored in a frame buffer. The dye is injected Quickly and rapidly as a bolus. Subsequent image frames are taken and stored and subtractively compared to produce difference images (e.g., one or two per second) using the inventive processing means. Initial visualization of the dye will appear in the difference image first in tumor tissue because the dye perfuses more rapidly into tumor tissue. Solid tumor margins will be the first images to appear in the difference frame as darkened lines outlining a solid tumor mass. This difference frame can be frozen and stored to allow the surgeon to study the tumor image and identify tumor margins in real time during an operation. Moreover, the dye will remain for a longer period of time in tumor tissue compared to normal tissue. Therefore, after there is general appearance of the dye throughout the area of interest in both normal tissue and tumor tissue, the dye clearance in tumor tissue will be delayed, allowing another opportunity to visualize tumor margins by dye presence in tumor tissue but not in normal tissue. In more aggressive or malignant tumors, the higher the tumor grade, the longer the dye remains in tumor tissue. For lower grade or more benign tumors, the dye remains in tumor tissue for 45 sec to 2 rain, whereas the dye can remain in more malignant tumors for up to 10 minutes.

The inventive method is superior to established tumor imaging techniques, such as MRI (magnetic resonance imaging) because optical imaging can distinguish low grade tumors that cannot be distinguished with current MRI techniques (MRI is not an intraoperative technique) and updated images are continually available during a surgical procedure by readministering the dye.

The dye can be administered on multiple occasions during a surgical procedure after resection has begun to look at resected walls for residual tumor tissue. For CNS tumors, MRI techniques require an advanced stage tumor that has compromised the blood brain barrier to be able to image such a tumor. The present optical imaging method, by contrast, can image even low grade tumors that have not yet compromised the blood brain barrier. Therefore, optical imaging is a more sensitive technique than MRI, can be used intraoperatively, and provides an approximate means for grading tumors.

The dye can be any emr-absorbing dye that is safe for ilt vivo administration, and has a short half-life when administered intravenously or intraarterially. Preferably, the dye tends to cross the blood brain barrier. Example of such a dyes are indocyanine green, Photofrin ®, NPe$_6$, BPD, and combinations thereof. Further, during surgical resection of a solid tumor, it is important that the dye be rapidly cleared from the area of interest. In that way, there can be repeated dye administrations to determine residual tumor tissue during resection.

During an imaging study, it is important to continually update the averaged image frame to account for patient movement, particularly for an awake patient. This will account for circulating residual dye and patient movements or tissue movements due to surgical manipulation.

The present invention further provides a method for imaging of cortical functional areas and dysfunctional areas, such as those areas of severe epileptic activity. The method involves administering a sensory signal for mapping a particular cortical function, or identifying an area of hyperactivity that is the location of epileptic activity in an epileptic patient. An epileptigenic area of the cortex will be visualized as spontaneously more active and cart be imaged by the inventive apparatus using a method for mapping intrinsic signals of cortical activity.

The method for visualizing intrinsic signals involves stimulating cortical tissue with specific paradigms. Various paradigms include, for example, presenting pictures of objects to a patient and asking the patient to name the object to alter neuronal activity which will result in an associated intrinsic signal.

Another feature of the inventive apparatus and method is the ability to image peripheral nerve damage and scarring. Nerves of the central and peripheral nervous system (PNS) are characterized by the ability to regenerate after damage. During operations to repair damaged peripheral or cranial nerves, one can image areas of nerve damage by imaging areas of blockage of intrinsic signals. For example, the nerve is exposed in the area of interest. The nerve is stimulated upstream of the site of damage. The active nerve pathway is imaged by intrinsic signals in the processed difference frame after activation. The site of nerve damage or blockage is evidenced by an abrupt end or diminution to the intrinsic signal at the damage site. In this way, the surgeon is able to obtain real time information precisely where there is nerve damage and to correct the damage, if possible.

Moreover, the inventive apparatus and ability to image intrinsic signals can be used when there is a need to remove tumor tissue that is located surrounding or adjacent to nerve tissue. For example a tumor called an acoustic neuroma is usually located surrounding an auditory (hearing) nerve. It is often a difficult procedure to remove tumor tissue without severing the auditory nerve (a cranial nerve) and causing one ear to become deaf or damage the facial nerve that innervates muscles that move the face. The inventive methods provide an ability to distinguish tumor tissue from surrounding nerve tissue using a dye. Additionally, the inventive method can continually provide information to the surgeon showing the precise location of the auditory or facial nerve by continually or periodically stimulating the nerve with a sound paradigm for the auditory nerve, or backfiring the facial nerve from a facial muscle, and detecting the intrinsic signal associated with nerve activity. Accordingly, when there is tumor tissue in close proximity to nerve tissue, one can use both the ability to locate tumor tissue with a dye and to locate nerve tissue by detecting intrinsic signal using the same imaging apparatus.

The imaging method can obtain information at the surface of an area of interest or can target an area of interest at a level deeper in tissue. Longer wavelengths of emr used to form the image (averaged control image and subsequent averaged images) can be used to probe areas of interest which are deeper into tissue. Moreover, if a difference image is created between the image seen with 500 nm emr and the image seen with 700 nm emr, the difference image will show an optical slice of tissue. Moreover, instead of using cutoff filters, administration of a dye can act as a tissue filter of emr to provide a filter in the area of interest. In this instance, it is desirable to utilize a dye that remains with tumor or normal tissue for a prolonged period of time.

The present invention further comprises a method for enhancing sensitivity and contrast of the images obtained from tumor tissue or intrinsic signal difference images, comprising: (a) illuminating an area of interest with a plurality of wavelengths of emr, wherein there is at least a first wavelength of emr and a second wavelength of emr; (b) obtaining a series of frames corresponding to each wavelength of emr, wherein a first sequence of frames is from the first wavelength of emr, the second sequence of frames is from the second wavelength of emr and so on; (c) processing the first sequence of frames into a first averaged control image, the second sequence of frames into a second averaged control image and so on; (d) stimulating for intrinsic signals or administering a dye for tumor tissue imaging; (e) obtaining a first series of subsequent frames using the first wavelength of emr, a second series of subsequent frames using the second wavelength of emr, and so on, and processing the first, second and so on subsequent series of frames into the first, second and so on subsequent averaged images, respectively; (f) obtaining a first difference image by subtracting the first averaged control image from the first subsequent averaged image and a second difference image by subtracting the second averaged control image from the second subsequent averaged image, and so on; and (g) obtaining an enhanced difference image by ratioing the first difference image to the second difference image. This can be accomplished, for example, with two single wavelength sources of emr, or by using a broad multiple wavelength source of emr and a plurality of longpass filters. Preferably, the monochromatic emr to illuminate the area of interest are from laser sources.

The inventive apparatus and methods for imaging intrinsic signals and tumor tissue can operate outside of a surgical procedure setting. More specifically, it is possible to obtain tissue imaging through intact skin and bone. In some areas of the body longer wavelength visible light and near infrared emr can easily pass through such tissue for imaging, such as breast tissue. With dye injection, areas of increased vascularity, such as tumor tissue can be identified.

Yet another aspect of the inventive method involves using an emr absorbing or fluorescent dye conjugated to a targeting molecule, such as an antibody, or more particularly, a monoclonal antibody or fragment thereof specific for an antigen surface marker of a tumor cell. The area of interest is illuminated with emr containing excitation wavelengths of the fluorescent dye but not emission wavelengths. This can be accomplished by use of a cutoff filter over the emr source. Preferably, the CCD camera is coupled to an image intensifier or micro channel plate (e.g., KS-1381 Video Scope International, Wash DC) to increase the sensitivity of the system by several orders of magnitude and allow for visualization of cells having fluorescent dyes attached hereto. Examples of fluorescent dyes that can be conjugated to a targeting molecule include, for example, Cascade Blue, Texas Red and Lucifer Yellow CH from Molecular Probes Eugene OR.

EXAMPLE 1

This example illustrates optical changes induced in five human subjects by direct cortical electrical stimulation or by stimulation paradigms during surgery for intractable epilepsy. Surface electrical recordings (surface EEG, ECOG) were correlated with optical changes. In FIG. 1A, the surface EEG (r) and stimulating (s) electrodes were placed just anterior to the face motor cortex. Four successive stimulations were followed by epileptiform afterdischarge episodes of different intensity and duration (bottom traces of FIG. 1B for surface EEG recording during stimulations #2 and #4). The spatial extent of activation and amplitude of optical changes at specific sites were compared for the four stimulations.

All imaging procedures reported in this example and the patient consent form were reviewed and approved by the University of Washington Human Subjects Review Committee. All patients signaled an informed consent statement for both the surgery and the imaging experiments. The cortex was evenly illuminated by a fiberoptic emr passing through a beam splitter, controlled by a D.C. regulated power supply (Lambda, Inc.) and passed through a 695 nm longpass filter. Images were acquired with a CCD camera (COHU 6500) fitted to the operating microscope with a specially modified cineadaptor. The cortex was stabilized with a glass footplate. Images were acquired at 30 Hz and digitized at 8 bits (512×480 pixels, using an Imaging Technology Inc. Series 151 sustem, Woburn Mass.). Geometrical transformations were applied to images to compensate for small amounts of patient motion (Wohlberg, *Digital Imaging Warping*, I.E.E.E. Computer Society, Los Alamatos, Calif., 1988). Subtraction of images collected during the stimulated state (e.g., during cortical surface stimulation, tongue movement, or naming) from those collected during a control state with subsequent division by a control image resulted in percentage difference maps. Raw data (i.e., no digital enhancement) were used for determining the average optical change in specified regions (average sized boxes was 30×30 pixels or 150-250 um$^2$). For pseudocolor images, a linear low pass filter removed high frequency noise and linear histogram transformations were applied. Noise was defined as the standard deviation of fluctuations in sequentially acquired control images as 0.003-0.009.

The optical changes between the stimulating electrodes (site #1 in FIG. 1A) and near the recording electrode (site #2) showed a graded response to the intensity and duration of each afterdischarge episode (FIG. 1B). The spatial extent of the epileptiform activity was demonstrated by comparing a baseline image collected before stimulation (FIG. 1A2) to those obtained immediately after stimulation. The intensity and spread of the optical changes were much less following stimulation #2 (shortest least intense afterdischarge episode, FIG. 1A3) than after stimulation #4 (longest most intense afterdischarge episode, FIG. 1-A4).

When the optical changes were below baseline, the surface EEG recordings did not identify epileptiform activity (n=3 patients) At site #3 in FIG. 1A1, the optical changes after stimulation were below baseline (i.e., black regions in FIG. 1A3). However, during the fourth stimulation, the epileptiform activity spread into the area of site #3 and the optical signal did not go below baseline until later (site #3, FIG. 1B). This negative optical signal likely represents inhibited neuronal populations (an epileptic inhibitory surround), decreased oxygen delivery, or blood volume shunted to activated regions.

Figure 2C:
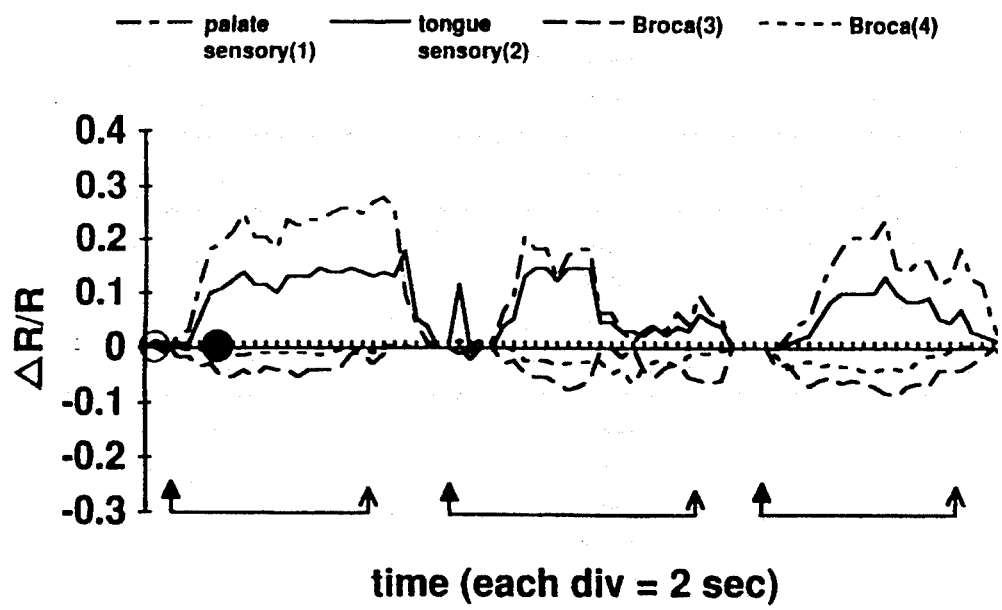
FIG. 2C shows when this image was taken.
Figure 2D:
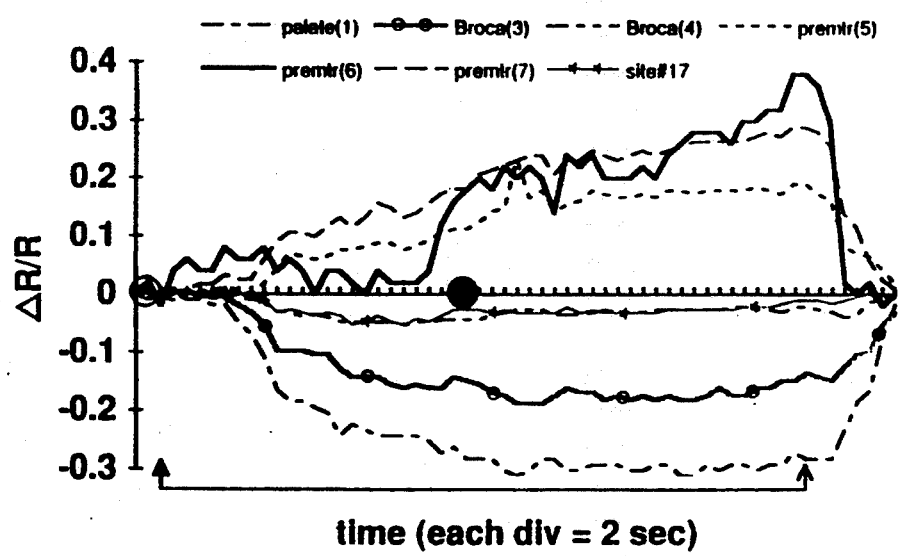
FIG. 2D shows the percentage difference changes from sites labeled in FIG. 2B1 and shows significant increases in the premotor cortex (sites #5, #6, and #7). Significant optical changes in the opposite direction occurred in the sensory cortex (site #1) and at site #3. The premotor region also showed temporal differences in activation., with the center area (site #6) increasing first and the regions above site #7 and below site #5 increasing later.

In FIG. 2, stimulation mapping of the cortical surface was performed on awake patients under local anesthesia to identify sensory/motor cortex and Broca's areas (FIG. 2A1 and B1). Broca's areas were defined as areas (i.e., sites #3 and #4) where speech arrest occurred during cortical stimulation. Images were collected during rest and while the patient moved their tongue side-to-side with their mouth closed. In three successive trials (FIG. 2C), the optical changes were greatest at cortical sites where stimulation evoked sensations in the palate (site #1 FIG. 2A1) and tongue (site #2, FIG. 2A1) with n=2 patients. The spatial extent of the optical changes were compared to an image obtained during tongue movement (FIG. 2A3). These results agree with those data reported by Lee et al. (*Ann. Neurol.* 20:32, 1986) who reported large electrical potentials in the sensory cortex during finger movement. The magnitude of the optical changes in the sensory cortex during tongue movement (10-30%) parallels sensory/motor cortex studies where cerebral blood flow increases 10-30% during motor tasks (Colebatch et al., *J. Neurophysiol.* 65:1392, 1991). Further, utilizing Magnetic Resonance Imaging (MRI) of blood volume changes in human visual cortex during visual stimulation, investigators have demonstrated increases of up to 30% in cerebral blood volume (Belliveau et al., *Science* 254:716, 1991).

Optical images were obtained from this same cortical region (i.e., area of interest) while the patient viewed blank slides and while naming objects on slides presented every two seconds. Percentage difference maps obtained during naming showed activation of the premotor area (baseline is FIG. 2B2, naming is FIG. 2B3). The sites of speech arrest (sites #3 and #4) and palate tingling (site #1) were identified by surface stimulation and demonstrate optical signals going in the opposite direction (black areas in FIG. 2B3). The area of activation was clearly different from that evoked by tongue movement without speech production (compare FIG. 2A3 to FIG. 2B3).

The optical images of premotor cortex activation during naming were in similar locations to the cortical areas identified in PET single word processing studies (Peterson et al., *Nature* 331:585, 1991; and Frith et al., *J. Neuropsychologia* 29:1137, 1991). The optical changes were greatest in the area of the cortex traditionally defined as Broca's area (posterior portion of the inferior frontal gyrus, that is sites #5, #6 and #7 in FIG. 2B1) and not in areas where electrical stimulation caused speech arrest.

In three other patients, posterior essential language sites (Wernicke's areas) were identified with cortical stimulation mapping (Ojemann, *J. Neurosci.* 11:2281, 1991). Optical imaging during naming showed optical changes in these regions of the temporal lobe. In one patient, two essential language sites were identified with cortical stimulation (sites #1 and #2 in FIG. 3A). A possible secondary language site (#3) was also identified due to one naming error in three stimulations. Further evidence of this region's importance to language was shown when language deteriorated when the surgical resection neared this area.

Figure 3A:
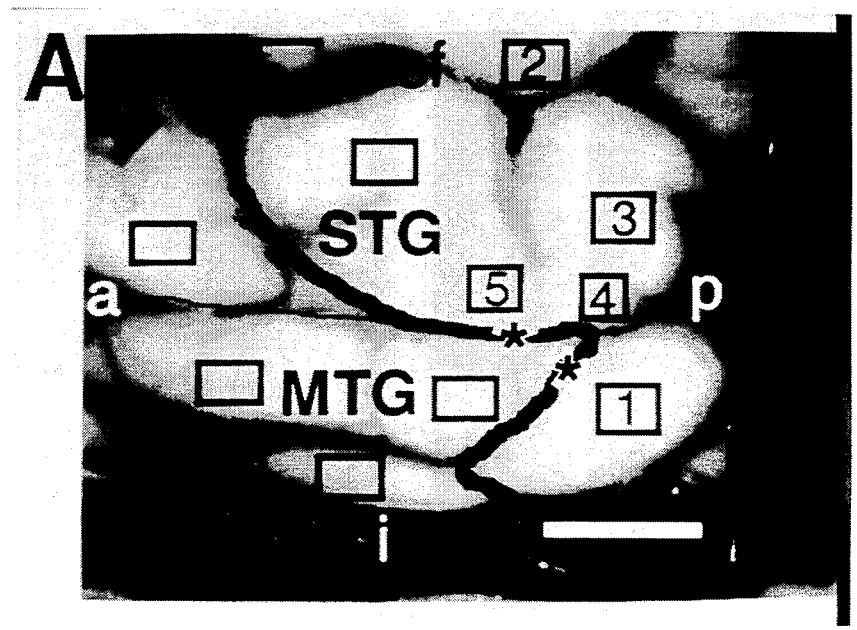
FIG. 3A shows an image of a cortical surface from a patient labeled for anterior (a), Sylvan fissure (sf), superior temporal gyrus (STG) and middle temporal gyrus (MTG). After the optical imaging, all cortical tissue to the left of the thick line was surgically removed. Sites #1 and #2 were identified as essential for speech (e.g., cortical stimulation blocked ability of subject to name objects). At site #3, one naming error in 3 stimulation trials was found. As the surgical removal reached the area labeled by the asterisks on the thick line, the patient's language deteriorated. All other unlabeled sites (FIG. 3A) had no errors while naming slides during cortical stimulation.
Figure 3B:
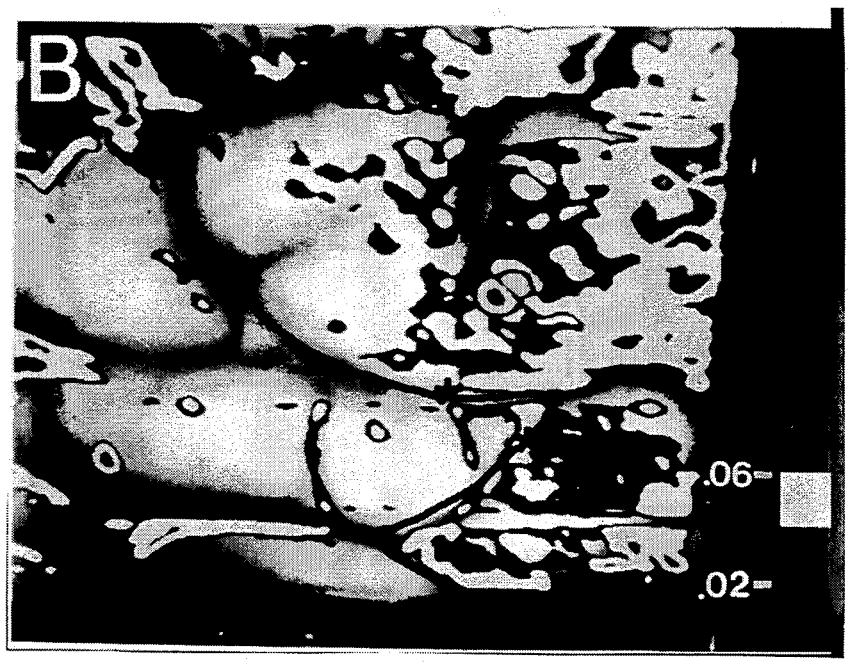
FIG. 3B shows an overlay of a difference image on the cortical analog image showing optical changes during naming (filled circle in FIG. 3C shows when image was collected). The magnitude of optical change is represented on the pseudocolor scale. The majority of the optical changes were in the region of essential and secondary language sites, but not in the more anterior cortex. Anteriorly, the optical changes were restricted to blood vessels.
Figure 3C:
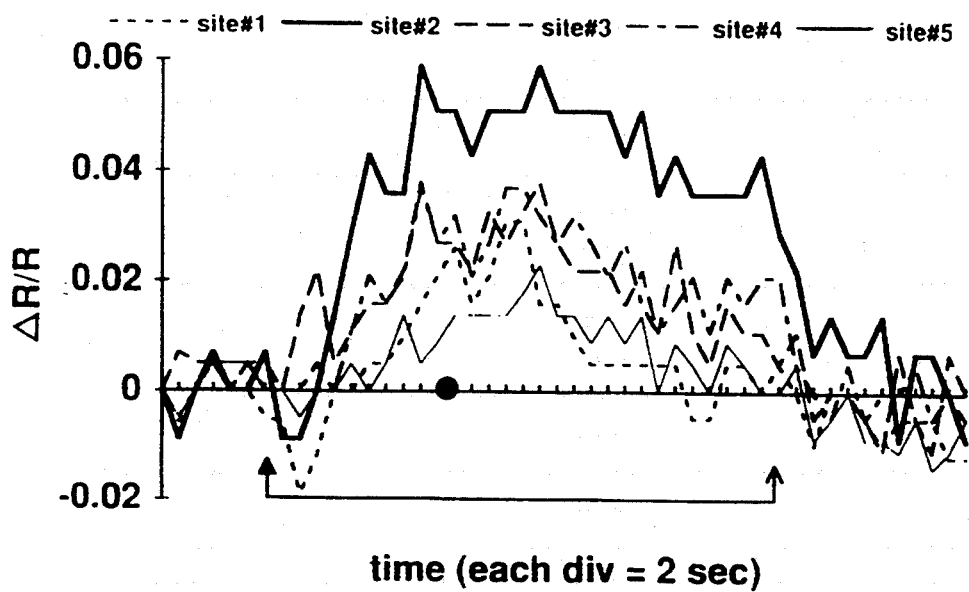
FIG. 3D shows the average percentage changes from the six unlabeled boxes in FIG. 3A. There were no significant increases or decreases at these more anterior sites.
Figure 3D:
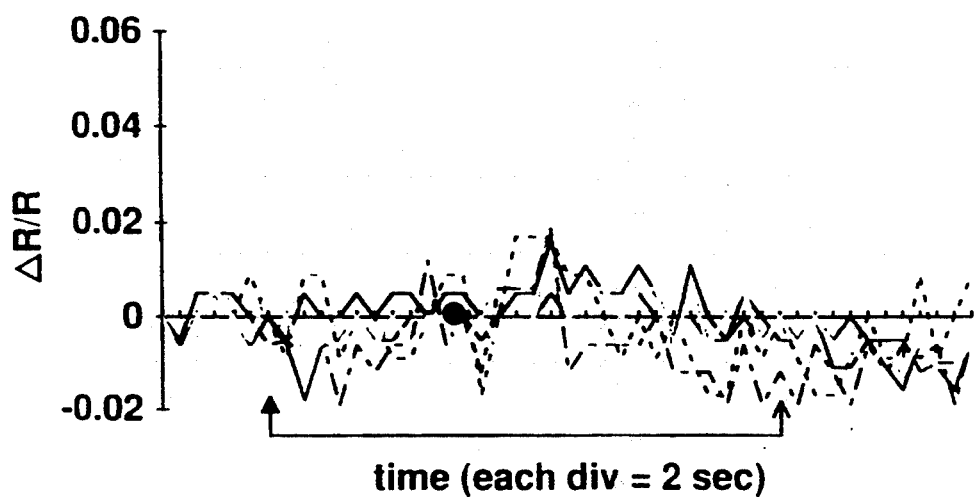

In FIG. 3B, optical changes during naming (same paradigm as in FIG. 2 naming study) were superimposed on the analog image of the cortical surface. Optical changes were found at essential (sites #1 and #2) and secondary language sites (#3, #4, and #5). The anterior cortical regions, without language disruption during cortical surface stimulation or actual removal, show no significant optical changes during naming except along blood vessels. At the boxes of essential and secondary language sites, the optical changes were significant (FIG. 3C). At the nonessential sites (unlabeled boxes in FIG. 3A) there were no optical changes in either direction (FIG. 3D). Cortical stimulation maps identify only essential cortex that must be preserved to prevent postoperative language deficits. These data demonstrate that optical imaging can also identify both essential and secondary language areas that must be preserved during neurosurgical procedures.

EXAMPLE 2

This example illustrates indocyanine green imaging of a low grade tumor. A MRI scan was conducted before the operation. Additionally, the patient was investigated for tumor tissue using the apparatus described according to the invention and specifically used in Example 1.

Figure 4A:
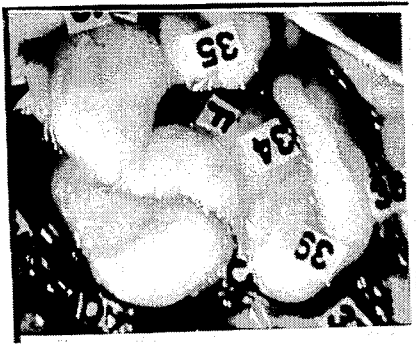
In FIG. 4A (upper left) the letters overlay the tumor as found by ultrasound, however tumors of this type and grade are notoriously difficult to distinguish from normal tissue once removal of the tumor begins.
Figure 4D:
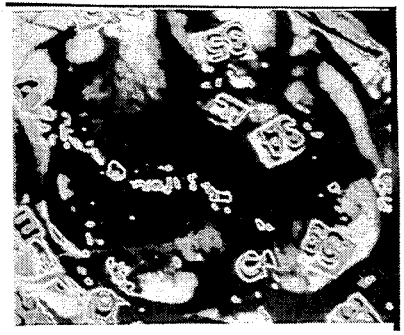
FIG. 4 shows a series of images from a patient having a low grade CNS tumor (astrocytoma, grade I).
FIG. 4B (middle left) shows a difference image taken about 15 sec after dye administration (indocyanine green 1 ug/kg).
FIG. 4C (lower left) shows the difference image about 30 sec after dye administration. The area of tumor tissue shows the first tissue staining. In this low grade tumor, all tissue (normal and abnormal) shows staining at 45 sec after dye administration as shown in FIG. 4D.
Figure 4B:
Figure 4E:
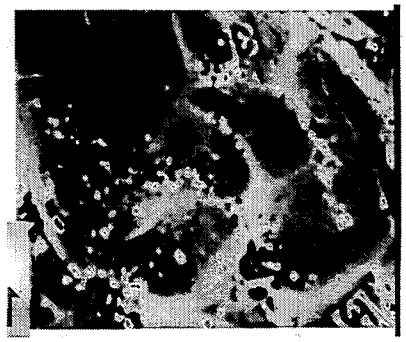
Figure 4C:
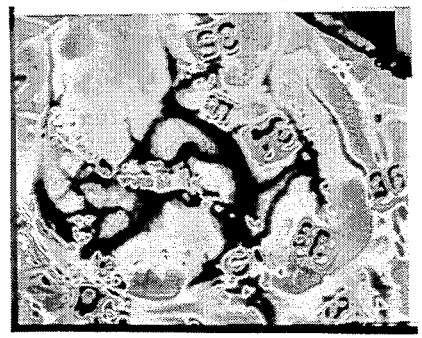
Figure 4F:

An averaged control image was obtained of the particular cortical surface area of interest and shown in FIG. 4A. Indocyanine green dye was administered into a peripheral intravenous catheter as a bolus at time 0. FIG. 4 shows a series of images from a patient having a low grade CNS tumor (glioma, grade I). In FIG. 4A (upper left) the letters overlay the tumor as found by ultrasound, however tumors of this type and grade are notoriously difficult to distinguish from normal tissue once removal of the tumor begins. FIG. 4B (middle left) shows a difference image taken about 15 sec after dye administration (indocyanine green 1 mg/kg). FIG. 4C (lower left) shows the difference image about 30 sec after dye administration. The area of tumor tissue is the first tissue stained. In this low grade tumor, all tissue shows staining at 45 sec after dye administration. FIG. 4D (upper right) is at 45 sec after dye, FIG. 4E (middle right) is one minute after dye administration and FIG. 4F (lower right) is five minutes after dye administration. These data show that tumor tissue takes up dye faster. Therefore, it is possible to image even low grade tumors by the inventive apparatus.

Subsequent pathology of this tumor tissue established it as a low grade glioma.

EXAMPLE 3

Figure 5A:
FIG. 5A (upper left) shows the visual image of this malignant brain tumor which was most malignant in the center and to the right (as was shown by pathology slides available one week after surgery) but was not malignant to the left.
Figure 5D:
FIG. 5 shows a series of images from the cortex of a patient with a malignant CNS tumor (glioblastoma; astrocytoma, Grade IV).
FIG. 5B (middle left) is the difference image at 15 sec after dye injection showing tissue looking like a low grade tumor surrounded by normal tissue. However at 30 sec (FIG. 5C, lower left), the normal tissue to the left is slightly more visible but malignant tissue is even more intense. After one minute (FIG. 5D, upper right) the initial intense staining in tumor tissue is maintained, and even remains at 10 minutes after dye in FIG. 5E (lower right). Therefore, it is possible to not only image the location of tumor tissue, but to also grade the tumor with more malignant tumors retaining dye for a longer period of time than a lower grade tumor.
Figure 5B:
Figure 5E:
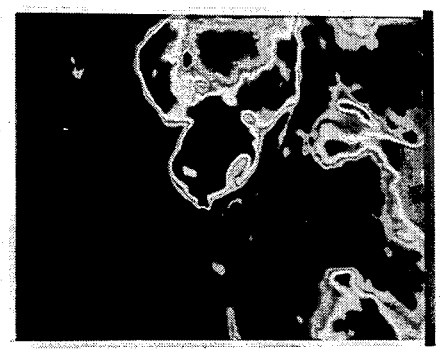
Figure 5C:
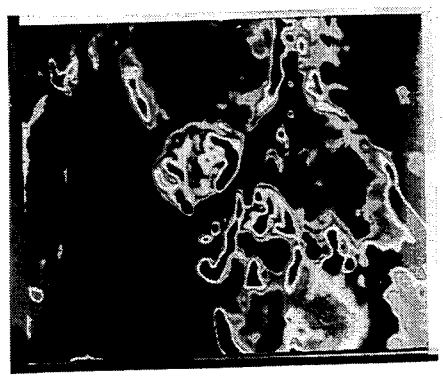

This example illustrates the image of a highly malignant CNS tumor (glioblastoma). A patient was imaged in a neurosurgical procedure as described in Example 1. The tumor imaging procedure was the same as in Example 2. FIG. 5 shows a series of images from the cortex of a patient. FIG. 5A (upper left) shows the visual image of this malignant brain tumor which was most malignant in the center (as was shown by pathology slides available one week after surgery) and was not malignant to the left but malignant to the right. FIG. 5B (middle left) is the difference image at 15 sec after dye injection showing tissue looking like a low grade tumor surrounded by normal tissue. However at 30 sec (FIG. 5C, lower left) the normal tissue to the left is slightly more visible but malignant tissue is even more intense. After one minute (FIG. 5D, upper right) the initial intense staining in tumor tissue is maintained, and even remains at 10 minutes after dye, in FIG. 5E (middle right). Thus, it is possible to not only image the location of tumor tissue, but also to grade the tumor with more malignant tumors retaining dye for a longer period of time than a lower grade tumor.

EXAMPLE 4

This example illustrates a series of images taken after resection of a malignant CNS tumor until the tissue appeared to be normal. This type of imaging of tumor margins provides a novel method of real-time imaging of tumor margins. After resection, the surgeon performed multiple histological margin sampling and when waiting for frozen section results, the images shown in FIG. 6 were obtained. FIG. 6 shows a series of images and difference images of an area of interest where a tumor was resected. The area of interest was thought to be free of tumor during the procedure. Normally, in the size of a tumor this patient had, only a single frozen sample would be taken for pathology analysis. In this case, before waiting for a pathology report based upon frozen sections (standard procedure), the images shown in FIG. 6 were obtained. FIG. 6A (upper left) is an analog image of the area of interest and FIG. 6C (upper right) shows the area of interest with histological markers. FIG. 6B (lower left) shows the post-dye difference image taken at one minute and at 10 minutes (FIG. 6D, lower right). Both post-dye difference images show a number of positive sites.

The neuropathological diagnosis one week after the operation revealed scattered tumor cells at sites 14, 17 and 16. These sites all correlate with increased optical imaging signals. Also significant is the fact that sites 13 and 15 were negative based upon optical imaging and upon neuropathological diagnosis. The area below and to the right of site 15 is also of interest. This site was positive for tumor tissue based upon optical imaging, but even with five times as many biopsy samples taken as in a normal procedure, the multiple histological margin sampling procedure missed this site.

EXAMPLE 5

This example illustrates a means for setting the CCD to optimize the apparatus to be able to detect signal with maximum sensitivity across a full dynamic range. The CPU should be programmed with software having the following features: (1) an output-analog signal, values of the image are close to saturating on the bright end (i.e., close to 225) are displayed as a distinct color, such as red; (2) values that are close to the dark end (i.e., are close to zero) are also displayed as a distinct color, such as blue. The following procedure is an example of an adjustment of the CCD camera.

1. With the gain and black-level on a camera-control box (CCB) initially set to 0, increase the emr intensity until the video signal is just saturating on the bright-end (i.e., some values in the, output-analog signal can be seen to be close to 255).
2. In crease the black-level on the CCB until the output image can be seen to be saturating on the dark end (i.e., some values in the output analog image can be seen to be close to 0).
3. Increase the gain on the CCB until some values of the output analog image can be seen to be saturating on the high end.
4. Iterate steps (2) and (3) until either (a) the gain is set to its maximum possible value, or (b) the black-level is set to its maximum possible value, or (c) the image is maximally enhanced across is full dynamic range (that is, no further adjustments of CCB gain, black-level or emr source will improve the image.
5. If in step (4) (a), the gain is set to its maximum level, or (b) the black-level is set to its maximum level, but the output image is still not maximally enhanced, then in the case of (a), decrease the setting on the CCB gain slightly, increase the emr source intensity until just saturating the bright end, and return to step (2). In the case of (b), decrease the setting of the black-level slightly, decrease the emr intensity, and return to step (3).

What is claimed is:

1. A method for imaging margins and dimensions of solid tumor tissue located in an area of interest, comprising:
   a. illuminating the area of interest with a source of electromagnetic radiation (emr) containing wavelengths of emr absorbed by a dye;
   b. obtaining a video signal of the area of interest as a sequence of frames and processing the sequence of frames into an averaged control image, wherein the image is a series of pixels;
   c. administering the dye by bolus injection into vasculature circulating to the area of interest;
   d. obtaining a series of subsequent frames of the area of interest over time and processing the series of subsequent frames into a subsequent averaged image, wherein the image is a series of pixels;
   e. comparing each subsequent averaged image with the processed averaged control image to obtain a series of difference images; and
   f. comparing each difference image for evidence of changed absorption within the area of interest which is the outline of solid tumor tissue, whereby tumor tissue is characterized by faster absorption of and longer retention of the dye.

2. The method of claim 1 wherein the dye is selected from the group consisting of indocyanine green, Photofrin ®, NPe$_6$, BPD, and combinations thereof.

3. The method of claim 1 wherein rates of change and magnitude of each pixel are compared by:
   a. determining a baseline value of each pixel for the wavelength of emr absorbed by the dye;
   b. administering the dye;
   c. obtaining a subsequent series of pixel values for a particular wavelength of emr;
   d. subtractively combining a first averaged image frame from a subsequent averaged image to provide a difference image; and
   e. superimposing the difference image onto an analog image.

4. The method of claim 3 further comprising color coding the difference image according to intensities of each pixel in the difference image.

5. The method of claim 1 wherein the source of emr is selected from the group consisting of high intensity light, diffuse or uniform visible light, infrared emr, and combinations thereof.

6. A method for imaging a solid tumor tissue located in an area of interest wherein the area of interest is located underneath intact skin and/or bone, comprising:
   a. illuminating the: area of interest with infrared region of electromagnetic radiation (emr);
   b. obtaining a video signal of the area of interest as a series of frames and processing the series of frames into an averaged control image, wherein the image is a series of pixels;
   c. administering a ,dye by bolus injection into vasculature circulating to the area of interest, wherein the dye absorbs emr in the infrared region of emr that is capable of penetrating through skin and bone tissue;
   d. obtaining a series of video images of the area of interest over time as a subsequent series of frames and processing each subsequent series of frames into a subsequent averaged image, wherein the image is a series of pixels;
   e. comparing each subsequent frame with the processed averaged control frame to obtain a series of difference images; and
   f. comparing each difference image for evidence of changed absorption within the area of interest which is the outline of solid tumor tissue, whereby tumor tissue is characterized by faster absorption of and longer retention of the dye.

7. The method of claim 6 wherein the dye is selected from the group consisting of indocyanine green, Photofrin ®, NPe$_6$, BPD, and combinations thereof.

8. The method of claim 6 wherein the changes in absorption rates of each pixel are compared by:
   a. determining a baseline value of each pixel for the wavelength of emr absorbed by the dye;
   b. administering the dye;
   c. obtaining a subsequent series of pixel values for the particular wavelength of emr;
   d. subtractively combining a first average image frame from a subsequent image to provide a difference image; and
   e. superimposing the difference image onto an analog image.

9. The method of claim 8 further comprising color coding the difference image according to intensities of each pixel in the difference image.

* * * * *

UNITED STATES PATENT AND TRADEMARK OFFICE
CERTIFICATE OF CORRECTION

PATENT NO. : 5,438,989

DATED : August 8, 1995

INVENTOR(S) : Daryl Hochman and Michael M. Haglund

It is certified that error appears in the above-identified patent and that said Letters Patent is hereby corrected as shown below:

Col. 7, line 13, change "A2" to "A1".

Col. 7, line 30, change "cator" to "color".

Col. 8, line 65, change "1E" to "4E".

Col. 10, line 64, change "reinappeal" to "remapped".

Col. 12, line 2, change "germanlure" to "germanium".

Col. 14, line 41, change "ALLY" to "ALU".

Col. 16, line 60, change "rain" to "min".

Col. 17, line 13, change "ilt" to "in".

Col. 17, line 36, change "cart" to "can".

Signed and Sealed this

Twelfth Day of November, 1996

Attest:

BRUCE LEHMAN

Attesting Officer

Commissioner of Patents and Trademarks